(12) United States Patent
Schurad et al.

(10) Patent No.: US 11,013,697 B2
(45) Date of Patent: May 25, 2021

(54) TRANSDERMAL THERAPEUTIC SYSTEM WITH AN OVERTAPE COMPRISING TWO ADHESIVE LAYERS

(71) Applicant: Luye Pharma AG, Miesbach (DE)

(72) Inventors: Björn Schurad, Munich (DE); Marieke Gosau, Unterhaching (DE)

(73) Assignee: Luye Pharma AG, Miesbach (DE)

(*) Notice: Subject to any disclaimer, the term of this patent is extended or adjusted under 35 U.S.C. 154(b) by 389 days.

(21) Appl. No.: 15/549,185

(22) PCT Filed: Mar. 14, 2016

(86) PCT No.: PCT/EP2016/055455
§ 371 (c)(1),
(2) Date: Aug. 7, 2017

(87) PCT Pub. No.: WO2016/146585
PCT Pub. Date: Sep. 22, 2016

(65) Prior Publication Data
US 2018/0028465 A1    Feb. 1, 2018

(30) Foreign Application Priority Data
Mar. 13, 2015 (EP) .................................. 15159068

(51) Int. Cl.
*A61K 9/70* (2006.01)
*A61K 31/485* (2006.01)
*C09J 7/38* (2018.01)
*C09J 7/22* (2018.01)
(Continued)

(52) U.S. Cl.
CPC .......... *A61K 9/7061* (2013.01); *A61K 31/485* (2013.01); *A61K 47/32* (2013.01); *C09J 7/22* (2018.01); *C09J 7/38* (2018.01); *C09J 133/08* (2013.01); *C09J 2301/122* (2020.08); *C09J 2301/302* (2020.08); *C09J 2400/20* (2013.01); *C09J 2423/006* (2013.01);
(Continued)

(58) Field of Classification Search
None
See application file for complete search history.

(56) References Cited

U.S. PATENT DOCUMENTS

| 4,710,191 A | 12/1987 | Kwiatek et al. |
| 5,662,925 A | 9/1997 | Ebert et al. |

(Continued)

FOREIGN PATENT DOCUMENTS

| DE | 102 23 835 A1 | 12/2003 |
| DE | 10 2014 007 650 A1 | 11/2014 |

(Continued)

OTHER PUBLICATIONS

PCT/EP2016/055455—International Search Report, dated May 2, 2016.
(Continued)

*Primary Examiner* — Robert A Wax
*Assistant Examiner* — Randeep Singh
(74) *Attorney, Agent, or Firm* — Curatolo Sidoti Co., LPA; Salvatore A. Sidoti; Floyd Trillis, III

(57) ABSTRACT

The present invention relates to a transdermal therapeutic system for administration of an active ingredient and a process for the preparation thereof. The transdermal therapeutic system comprises an overtape with two adhesive layers.

18 Claims, 1 Drawing Sheet

(51) Int. Cl.
*A61K 47/32* (2006.01)
*C09J 133/08* (2006.01)
(52) U.S. Cl.
CPC ...... *C09J 2433/00* (2013.01); *C09J 2433/006* (2013.01); *C09J 2467/001* (2013.01); *C09J 2467/006* (2013.01); *C09J 2483/005* (2013.01)

(56) References Cited

U.S. PATENT DOCUMENTS

| | | | | |
|---|---|---|---|---|
| 6,010,715 | A * | 1/2000 | Wick | A61K 9/7084 |
| | | | | 424/448 |
| 6,436,433 | B1 * | 8/2002 | Muller | A61K 9/7061 |
| | | | | 424/448 |
| 2010/0178323 | A1 | 7/2010 | Kydonieus et al. | |
| 2013/0331803 | A1 * | 12/2013 | Fleschhut | A61K 9/7061 |
| | | | | 604/307 |

FOREIGN PATENT DOCUMENTS

| | | |
|---|---|---|
| EP | 0 430 019 A2 | 6/1991 |
| GB | 2 184 016 A | 6/1987 |
| WO | WO 96/19205 A1 | 6/1996 |
| WO | WO 99/12529 | 3/1999 |
| WO | WO 02/074286 A1 | 9/2002 |
| WO | WO 03/047556 A1 | 6/2003 |
| WO | WO 2012/065740 A1 | 5/2012 |

OTHER PUBLICATIONS

PCT/EP2016/055455—International Written Opinion, dated May 2, 2016.

* cited by examiner

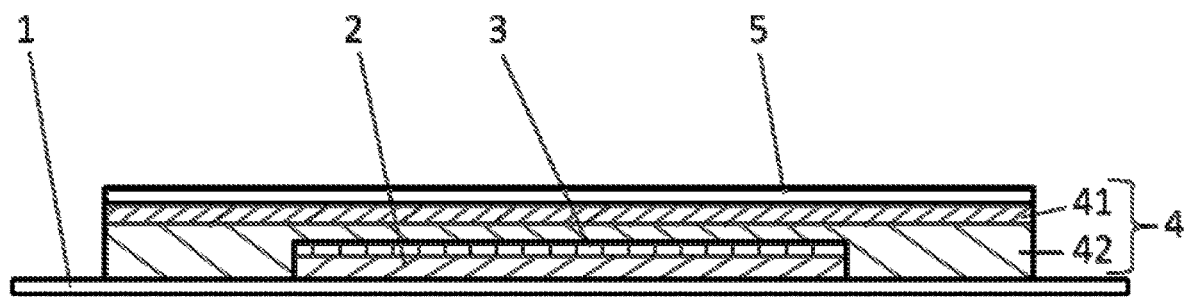

TRANSDERMAL THERAPEUTIC SYSTEM WITH AN OVERTAPE COMPRISING TWO ADHESIVE LAYERS

CROSS REFERENCE TO RELATED APPLICATIONS

This application is a national stage application of International Application No. PCT/EP2016/055455, filed 14 Mar. 2016, which claims priority from European Patent Application No. 15159068.4, filed 13 Mar. 2015, which applications are incorporated herein by reference.

The present invention relates to a transdermal therapeutic system for administration of an active ingredient and a process for the preparation thereof. The transdermal therapeutic system (TTS) comprises an overtape comprising two adhesive layers. The TTS combines several excellent properties relevant to such a system, in particular it does not cause sensation of a foreign body on the skin while at the same time it has good adhesive properties over a prolonged period so that the TTS is particularly suitable for the continuous administration of an active ingredient over several days. In particular, the adhesiveness of the TTS does not deteriorate during storage.

Transdermal drug application, which is in most cases effected by a transdermal therapeutic system such as a transdermal patch, offers distinct advantages over conventional administration methods. For example, some drugs cannot be absorbed from the digestive tract after oral administration. Systemic first-pass metabolism upon oral administration also calls for other modes of administration. Intravenous and subcutaneous administration by injection is hampered by the disadvantage of being painful and invasive. Especially for the non-acute, long term treatment with active ingredients transdermal administration offers the advantage of high systemic bioavailability combined with a relative convenient use (e.g. no painful injection necessary) resulting in improved reliability and patient compliance. Furthermore, as generally with controlled release dosage forms, administration of a drug with a transdermal therapeutic system is advantageous in order to obtain more constant plasma levels, compared with an immediate release administration of the drug.

In most cases, a transdermal therapeutic system is a transdermal patch, i.e. a small adherent bandage containing the active ingredient to be delivered. These bandages can have various forms and sizes. The simplest type is an adhesive polymer matrix comprising an active ingredient (reservoir) with a backing layer on one side and a protective layer (release liner) on the other side, which is removed before the system is applied to the skin where it should adhere for the intended period of application. The intended period of application of TTS over which the contained active ingredient should be delivered is often 24 hours or even longer such as 3 or 7 days. Application of an active ingredient by a TTS over several days is convenient for patients who need long term treatment and can reduce the risk of mistakes which can e.g. happen in a hospital setting when frequent (daily) renewal is required.

An important property of TTS, especially of TTS worn for a longer time period, is proper adherence to the skin. Failing that, the TTS becomes loose or even falls off the skin before the end of the intended period of application. Continuous contact of the TTS with the skin surface is, however, necessary to ensure continuous and constant administration of the predetermined dose of the active ingredient. Unnoted loss of the TTS can even endanger others when the TTS, which still contains active ingredient, is found by them and handled without precaution.

A further significant problem with transdermal therapeutic systems is that the adhesiveness can decrease during storage. Thus, even if a TTS immediately after its preparation has a suitable adhesiveness, it is a well-known problem that even after a few weeks of storage the adhesiveness can be significantly decreased.

The afore described aspects are particularly relevant when the TTS contains highly potent active ingredients such as opioids like buprenorphine, which have a very low therapeutic index and under- or overdosing can lead to severe impairment of the patient. The active ingredients are also expensive so that they should be used very efficiently.

In the simplest form of a TTS the pressure-sensitive adhesive polymer matrix containing the active ingredient adheres to the skin of a patient. However, the delivery of the active ingredient from the pressure-sensitive adhesive to the skin of the patient depends on the type and composition of the adhesive polymer matrix. It should be noted that the diffusion of the active substance through the human skin can only be achieved in solubilized form. This often proves to be problematic. With a low drug loading in the polymer matrix, the drug release from the system might not be sufficient and a higher drug load can negatively affect the adhesiveness of the patch. If the drug load is beyond the limit of solubility, this can lead to crystallization of the drug and thus does not allow a predictable or defined drug delivery. Furthermore, solid particles which can be formed by recrystallization of the drug due to excessive loading, can significantly affect the adhesive properties of the TTS and can cause skin irritation.

With some active ingredients, it is thus difficult to find an adhesive polymer matrix which can dissolve sufficient active ingredient, deliver sufficient active ingredient to the skin, provide sufficient adhesiveness even after storage and which is considered as being pleasant by the patient. In such cases, e.g. an additional adhesive layer is applied on the adhesive polymer matrix or a so called overtape is used which is in essence a backing layer comprising an adhesive layer which extends beyond the adhesive polymer matrix. In a system with an overtape the formulator has much more freedom in selecting an adhesive polymer matrix for delivering the active ingredient, because the adhesion is mainly controlled by the overtape. The above problems of finding suitable adhesive polymer matrices occur with many opioids and the inventors found that in particular buprenorphine benefits from the use of an overtape.

A simple system for the constant transdermal delivery of buprenorphine, an opioid analgetic with a low oral bioavailability, is described in EP 0 430 019. According to EP 0 430 019 the polymer of the buprenorphine reservoir layer is preferably a block-polymer based on styrol and 1,3-butadiene, polyisobutylene or an acrylate and/or methacrylate polymer. The backing layer can be a flexible or inflexible material. It can be made of polymeric or metal foils, such as aluminum foil which may be used alone or coated with a polymeric substrate. Textile fabrics may be used, too. Preferred is a composite material of an aluminized foil.

WO 99/12529, however, describes that the mentioned backing layer materials of EP 0 430 019 arouse a sensation of a foreign body on the skin, which is unpleasant to the user.

The document tries to find a backing layer material which avoids this problem. WO 99/12529 furthermore mentions the problem of "curling", which is also related to the properties of the backing layer material. The curling effect occurs during production of the TTS. When the individual patches are punched from the laminate, the material of the backing layer comes under tensile stress and the resulting elastic return force means that, during punching the opposite ends of the patches are each bent up. This leads to a high reject rate resulting in high costs and environmental burden.

In the attempt to solve above mentioned problems WO 99/12529 suggests to use a backing layer comprising a unidirectional elastic material having an elasticity of at least 20%. Most preferably the elasticity is between 44 and 56%. In a comparative example WO 99/12529 uses a bidirectional backing layer made of polyethylene terephthalate with an elasticity of 30% in cross and longitudinal direction.

DE 10 2014 007 650 provides a process for preparing transdermal patches which avoids the problem of "curling" reported in WO 99/12529 when bielastic backing layers are used.

WO 03/047556 is primarily directed to a TTS that can be exposed to water, but it also describes the development of a pronounced unpleasant sensation of a foreign body caused by the rigidity of a TTS, especially the backing layer. According to WO 03/047556 the rigidity of one component (active ingredient-containing matrix, backing layer etc.) of the TTS may also result in the TTS becoming detached or even falling off the skin, because not only good adhesive properties, but also sufficient flexibility of the TTS would be necessary for adequate adhesion of the TTS, because a TTS should adapt to the movements of the skin. WO 03/047556 suggests the use of a flexible backing material. By "flexible" the ability is meant to bend easily when exposed to a small force directed perpendicularly onto the layer. According to WO 03/047556 the backing layer may also be elastic which would be important for wearing comfort. "Elastic" in the sense of WO 03/047556 refers to the capability of stretching in at least one direction to at least 10%, preferably at least 30%.

There is still a need for the provision of further or even better transdermal therapeutic systems with a favorable combination of properties. Such properties e.g. include effective production of the TTS, no foreign body sensation caused by the TTS during wear while good adhesive properties of the TTS even after storage should be provided by one and the same TTS. Other desirable properties include a well-controlled release of active ingredient over a prolonged period of time to reach desired plasma levels over such period. These properties become more difficult to achieve when the drug containing polymer matrix of the TTS is not sufficiently adhesive itself (i.e. the simplest form of TTS cannot be used).

It was now surprisingly found that the adhesiveness after storage of patches with an overtape can be significantly improved, if the pressure-sensitive adhesive layer (which is part of the overtape) is composed of at least two layers, a first layer which contacts the backing layer of the overtape and a second layer which is for contacting the skin of the patient and before the patch is applied, contacts the release liner. The patches of the present invention solve the problems above, they combine the properties of avoidance of foreign body sensation of the TTS on the skin, provide good adhesive properties over a prolonged period and have a low reject rate during TTS production. In particular, such a TTS is advantageous, because the adhesive strength is essentially (e.g. ±20% preferably ±10%) constant during storage, preferably during storage at 25° C. over at least 2 weeks.

The present invention is thus directed to:
A transdermal therapeutic system comprising
a) a release liner (1),
b) a core comprising
b1) a polymer matrix layer (2) containing an active ingredient and
b2) a separating layer (3) and c) an overtape comprising
c1) a pressure-sensitive adhesive layer (4) and
c2) a backing layer (5)
wherein the overtape c) and the release liner (1) extend beyond the core at all sides of the core
characterized in that the pressure-sensitive adhesive layer comprises a first layer (41) which is in contact with the backing layer (5) and comprises a first pressures-sensitive adhesive polymer and a second layer (42) which is in contact with the release liner (1) and comprises a second pressure-sensitive adhesive polymer, wherein the second pressure-sensitive adhesive polymer is a silicone polymer or a non-crosslinked polyacrylate (preferably, the second pressure-sensitive adhesive polymer is a non-crosslinked polyacrylate) and the first pressure-sensitive adhesive polymer is different from the second pressure-sensitive adhesive polymer.

The construction of a preferred TTS according to the invention in cross-section is shown in FIG. 1. A core of the TTS comprises a polymer matrix layer (2) containing an active ingredient and a separating layer (3). The separating layer (3) is located at a side of the polymer matrix layer (2) that is in use opposite to the skin. An overtape comprising a backing layer (5) and a pressure-sensitive adhesive layer (4) on the side of the backing layer (5) that faces in use the human skin is arranged on the core and extends beyond the core at all sides of the core, more particularly on that side of the core where the separating layer (3) is located and on that side of the separating layer that is in use opposite to the skin. A release liner (1) is located at the side of the core that faces the skin and extends beyond the core at all sides of the core, more particularly the release liner (1) is located on that side of the core where the polymer matrix layer (2) is located and on that side of the polymer matrix layer (2) that faces the skin. Where the release liner (1) extends beyond the core it is located at the side of the pressure-sensitive adhesive layer (4) facing the skin in use. The release liner (1) is removed before use of the TTS. The pressure-sensitive adhesive layer (4) comprises (in FIG. 1 consists of—an embodiment which is preferred according to the invention) a first layer (41) which contacts the backing layer (5) and a second layer (42) which contacts the release liner (1) and when the patch is in use will contact the human skin. Both, first layer (41) and a second layer (42) forming part of the adhesive layer (4) extend beyond the core of the TTS.

Still, it is apparent from FIG. 1 that not all of the different layers of the TTS extend over the same area. After removal of the release liner of the TTS, adhesion to the skin is partially provided by that part of the pressure-sensitive adhesive layer surrounding the core.

In one embodiment, the TTS of the present invention is one wherein the pressure-sensitive adhesive layer (4) and the backing layer (5) extend at least 4 mm, preferably 4 to 30 mm, more preferably 5 to 20 mm and most preferably 6 to 15 mm beyond the core. Preferably, the pressure-sensitive adhesive layer (4) and the backing layer (5) extend at least 4 mm, preferably 4 to 30, more preferably 5 to 20 mm and most preferably 6 to 15 mm beyond the core at all sides of the core.

The total skin adhering surface area of the TTS of the present invention is preferably between 2.5 to 100 cm$^2$, more preferably between 5 to 60 cm$^2$, in particular between 10 to 60 cm$^2$. Even when the TTS of the present invention has a relatively large skin adhering surface area of ≥25 cm$^2$ (e.g. 25 to 50 cm$^2$) it does not cause a sensation of a foreign body on the skin.

In one embodiment, the core of the TTS of the present invention also comprises a membrane. The membrane is located between the active ingredient containing polymer matrix layer and the release liner. The main purpose of the membrane is to further control the release rate of the active ingredient from the TTS. So, differences in the permeability for the active ingredient through the skin can be balanced. Preferably, the membrane is a microporous membrane. Suitable membranes are known in the state of the art. In a preferred embodiment the membrane can contain or may be composed of polyethylene terephthalate, polyethylene, polypropylene or ethylene vinyl acetate. An especially preferred material for the membrane is a microporous polypropylene film. Optionally, the membrane can be pretreated according to known methods.

The thickness of the membrane is not particularly restricted and can e.g., be in the range of 10 µm to 100 µm, preferred less than 50 µm, e.g., about 25 µm. The pore size is preferably in the range of 0.001 to 0.025 µm$^2$, e.g., in the range of 0.002 to 0.011 µm$^2$, particularly about 0.005 µm$^2$. Also the shape of the pores is not particularly restricted, a rectangular shape is preferred. An example of a membrane is a microporous polypropylene film having a thickness of about 25 µm and a pore size of about 0.12 µm×0.04 µm, as marketed under the trade name Celgard 2400 from Celgard LLC, Charlotte, USA.

The active ingredient in the TTS of the present invention is preferably an opioid or a pharmaceutically acceptable salt thereof. The opioid can possibly also be in the form of an ether, ester or amide. Also a solvate can be used.

The opioid is preferably selected from the group consisting of buprenorphine, sulfentanil, hydromorphone, morphine, fentanyl, dextropropoxyphene, ethylmorphine, meptazinol, nalbuphine, pethidine, tilidin, butorphanol, dextromoramide, dezocin, ketobemidone, oxymorphone, pentazocine, diacetylmorphine, oxycodone, alfentanil, remifentanyl, phenoperidine, anileridine, diamorphine, piritramide, benzitramide, methadone, phenazocine, (1R, 2R)-3-(3-dimethylamino-1-ethyl-2-methyl-propyl)-phenol, (2R, 3R)-1-dimethylamino-3-(3-methoxy-phenyl)-2-methyl-pentan-3-ol, (1RS, 3RS, 6RS)-6-Dimethylaminomethyl-1-(3-methoxy-phenyl)-cyclohexane-1,3-diol, (1R, 2R)-3-(2-di methylaminomethyl-cyclohexyl)-phenol.

Pharmaceutically acceptable salts are preferably selected from the group consisting of acetate, bisulfate, bitartrate, citrate, fumarate, hydrobromide, hydrochloride, hydroiodide, lactate, laurate, malate, maleate, nitrate, oleate, palmitate, phosphate, stearate, succinate, sulfate, tartrate, and valerate. A particularly preferred salt is hydrochloride.

An opioid from the phenanthrene group, as buprenorphine or nalbuphine, and pharmaceutically acceptable salts thereof, or mixtures thereof are preferred to be used as active ingredient in the TTS of the present invention. A particularly preferred TTS of the present invention is a TTS wherein the active ingredient is buprenorphine.

In order to improve the effectiveness and tolerance of the TTS of the present invention, opioids with different pharmacodynamics and pharmacokinetics may also be combined in the TTS.

In the TTS the polymer matrix layer (the reservoir) has to contain an amount of active ingredient sufficient to induce the desired effect, e.g. analgesia, in a human being and to maintain it for a prolonged period. Preferably, the polymer matrix layer contains an amount of active ingredient sufficient to induce and maintain the desired effect, e.g. analgesia, for a period of at least three days, in particular three to seven days, especially preferred about 7 days.

The absolute amount of active ingredient to be employed depends on various factors, in particular the size of the TTS to be used and the duration of use. Preferably, the TTS contains the active ingredient, e.g. buprenorphine base, in an amount of 5 to 30% by weight, preferably of 5 to 20% by weight, more preferably in an amount of 5 to 15% by weight, most preferably 8-12% by weight based on the total weight of the polymer matrix layer including the active ingredient. Preferably, there result weights per unit area for the polymer matrix layer containing active ingredient ranging from 25 to 150 g/m$^2$, more preferably 50 to 120 g/m$^2$, in particular from 70 to 100 g/m$^2$.

When the term "total weight of the polymer matrix layer including the active ingredient" or an amount referring to the polymer matrix layer is used this means the dry weight, i.e. the weight of the polymer matrix layer containing an active ingredient in the ready-to-use patch, unless otherwise disclosed or apparent.

The backing layer (5) of the TTS of the present invention is not particularly restricted but preferably consists of an elastic material. Preferably, the backing layer is an elastic polyester fabric (or web), e.g. a polyethylene terephthalate fabric (or web) or elastic polybutylene terephthalate fabric (or web). Alternatively, the backing layer can also comprise or consist of polyurethane. The elasticity of the backing layer can be determined as disclosed in WO 99/12529 and thus according to DIN 61632, however, while WO 99/12529 considers that the backing layer must be an unidirectional elastic polyester fabric, the present invention can be applied to unidirectional as well as multidirectional, elastic backing material, e.g. a polyethylene terephthalate as used in comparative example 1 of WO 99/12529 or a multidirectional or bidirectional elastic polybutyl terephthalate. Multidirectional includes and preferably is bidirectional.

Thus, a specific embodiment of the invention comprises the use of multidirectional elastic material which is elastic in at least two directions, a longitudinal and a transverse direction. Oblique elasticity is the result of a superposition of elasticity in the transverse and longitudinal directions. Relative to the longitudinal axis of the structure, the transverse axis is that lying at a right angle to it. For purposes of the present invention, the terms "longitudinal direction" and "machine direction", are synonymous and referred to as "MD", as are the terms "transverse direction" and "cross machine direction", referred to as "CD". In a circular structure, the longitudinal and transverse axes are of course identical in length.

Preferably, the backing layer of the TTS of the present invention consists of a multidirectional elastic fabric with an elongation in MD of at least 10% and an elongation in CD of at least 10%. More preferably, the backing layer consists of a multidirectional elastic fabric with an elongation in MD of at least 30% and an elongation in CD of at least 30%.

In an alternative embodiment of the invention a unidirectional elastic material is used for the backing layer (6). Preferably, a unidirectional elastic fabric with an elongation in MD of less than 10% and an elongation in CD of at least 10% or vice versa is used. More preferably, the backing layer consists of a unidirectional elastic fabric with an elongation in MD of less than 6% and an elongation in CD of at least 30% or vice versa.

The thickness of the backing layer of the TTS of the present invention can e.g., be in the range of 10 µm to 900 µm. Preferably, the thickness of the backing layer of the TTS of the present invention is between 300 to 800 µm.

Examples of commercial products that can be used as backing layer according to the present invention are e.g. fabrics from KOB (Karl Otto Braun GmbH & Co. KG), article numbers 021, 104, 520, 051, 053 and 023 or nonwoven fabrics from Freudenberg (Vilmed® M 1573, Vilmed® M 1533, Vilmed® M 1506, Vilene® EW 9100, Vilene® EW 7900, Vilene® EW 9050, Vilene® EW 8600, Vilene® EW 6870). An example of a suitable polyurethane is the product 3M™ CoTran™ 9700.

The pressure-sensitive adhesive layer (4) allows for adhesion of the TTS to the skin. The pressure-sensitive adhesive layer must also allow the patch to be easily removed after the application time with no residues remaining on the skin and without irritating the skin. While it was found that many pressure-sensitive adhesives provide an initial good adhesiveness to the skin combined with a good removability, it was found that the adhesiveness of the patch can deteriorate significantly during storage. The adhesiveness of the patch also provides problems (which are solved by the present invention), if a specific polymer matrix layer (2) is used as reservoir as disclosed later on in this specification. This specific polymer matrix is excellent when it comes to administering an active ingredient (in particular buprenorphine or a pharmaceutically acceptable salt thereof) but makes it difficult to provide a patch having satisfactory adhesive and cohesive properties. In particular, with those polymer matrices it has been shown that the requirements of the adhesive which must provide a suitable adhesiveness to the skin (but, of course, it must also be possible to release the adhesive from the skin without damaging the skin or hurting the patient) and to the backing layer is difficult to achieve, in particular, if the adhesiveness should not deteriorate during storage of the patch.

In order to solve the above problems, the TTS of the present invention contains an adhesive layer (4) which comprises (preferably consist of) two layers, a first layer (41) which adheres to the backing layer (5) of the overtape and a second layer (42) which adheres to the release liner (1), and when the release liner is removed and the TTS is in use to the skin of the patient.

As used in the present specification, the term "polymer" is also intended to cover copolymers composed of two or more different types of monomers.

Preferably, the TTS has an adhesiveness of at least 2.0, more preferably at least 3.0, most preferably at least 4.0 N/25 mm (tested on stainless steel plate fixed horizontally (90° angle) to the measuring system, 2 kg for 1 min adhesion pressure). The measurements are made according to DIN- or ASTM-standards, e.g. DIN EN 1939 or ASTM D3330/D3330 M.

According to the invention, the pressure-sensitive adhesive polymer of the first pressure-sensitive adhesive layer (41) (also designated as "first pressure-sensitive adhesive polymer") is different from the pressure-sensitive adhesive polymer of the second pressure-sensitive adhesive layer (42) (also designated as "second pressure-sensitive adhesive polymer"). The second pressure-sensitive adhesive polymer is either a silicon polymer or a non-crosslinked polyacrylate and the first pressure-sensitive adhesive polymer is different from the second pressure-sensitive adhesive polymer.

The first pressure-sensitive adhesive polymer is not particularly restricted as long as it is different from the second pressure-sensitive adhesive polymer. Preferably, the first pressure-sensitive adhesive polymer has a lower adhesiveness than the second pressure-sensitive adhesive polymer. Methods for determining the adhesiveness of pressure-sensitive adhesive polymers are known in the art (e.g. as disclosed above), and according to the invention, any method that is suitable to measure the adhesiveness of a pressure-sensitive adhesive polymer can be used. Of course, for comparing the adhesiveness of the first and the second pressure-sensitive adhesive polymer, the same method must be used for both polymers. The first pressure-sensitive adhesive polymer has a lower adhesiveness than the second pressure-sensitive adhesive polymer, if one test as explained above results in a higher adhesiveness for the first pressure-sensitive adhesive polymer.

Preferably, the first pressure-sensitive adhesive polymer differs from the second pressure-sensitive adhesive polymer in that it is less prone for "cold flow". "Cold flow" is a phenomenon that a pressure-sensitive adhesive might creep or migrate under ambient storage conditions or especially under stress conditions. This well-known behavior to move like a thick, viscous liquid usually causes undesirable characteristics. It is based on the viscoelastic and rheological properties of the polymer and can be sufficiently estimated by measuring the shear force of the material. Adequate methods for determining the relevant parameters of pressure-sensitive adhesive polymers are known in the art and, according to the invention, any method that is suitable to assess the cold flow of a pressure-sensitive adhesive polymer can be used.

In a preferred embodiment, the first pressure-sensitive adhesive polymer is a polyisobutylene (PIB) or a polyacrylate (the term polyacrylate used herein is also intended to cover polymethacrylates and copolymers comprising at least 50% of monomer units resulting from acrylic acid or methacrylic acid or derivatives such as esters thereof).

In an alternative preferred embodiment, the first pressure-sensitive adhesive polymer is a polyacrylate (preferably a crosslinked polyacrylate), a polyisobutylene, a styrene-butadiene-styrene block copolymer or a styrene-butadiene copolymer.

Polyisobutylenes are known in the art. Preferably, the first pressure-sensitive adhesive polymer is a mixture of two or more polyisobutylenes with different molecular weights and has a weight-average molecular weight (as determined by GPC) of 20,000 to 1,500,000.

Polyacrylates which are suitable as first pressure-sensitive adhesive polymer are also known in the art. Suitable acrylic polymers are disclosed e.g. in WO 02/074286, paragraphs [0050] and [0051] the content of which is insofar incorporated by reference. Preferred are in particular copolymers of alkyl acrylate and/or alkyl methacrylate whose alkyl group has 1 to 12 carbon atoms, with a comonomer having functional groups. These copolymers included herein are polymeric compounds from acrylic acid esters, such as methyl methacrylate, ethyl acrylate, 2-ethylhexyl acrylate, hydroxyethyl acrylate, butyl acrylate, butyl methacrylate and isooctyl acrylate and e.g. consist of 50 to 95 weight-% of the principal acrylate or methacrylate monomer, 2 to 40 weight-% of a modifying monomer or monomer mixture and 2 to 20 weight-% of one or more monomers containing functional groups.

The first pressure-sensitive adhesive polymer can also be a polyacrylate containing carboxylic groups, but in this case the polyacrylate is crosslinked. In one embodiment of the present invention, the first pressure-sensitive adhesive polymer comprises carboxylic groups which are crosslinked. Such polyacrylates are known in the art and commercially available, and here it can be referred e.g. to the products (the first number in the product specification can either be 387 or 87, the products are the same) Durotak 87-2052, 87-2054, 87-2825, 87-2074, 87-2196, 87-2677, 87-2852, 87-2979 and 87-4350.

The second pressure-sensitive adhesive polymer is a polyacrylate which is not crosslinked. Preferably, the second pressure-sensitive adhesive polymer is a polyacrylate with carboxyl groups (i.e. with "COOH groups"), which is not crosslinked. The polyacrylates are as discussed above in connection with the first pressure-sensitive adhesive polymer, but with the proviso that the polyacrylate is not crosslinked and preferably contains carboxylic groups. Such pressure-sensitive adhesive polymers are commercially available, e.g. under the tradenames Durotak 87(or 387)-2051 and 87(or 387)-2353. In one embodiment of the present invention, the first and second pressure-sensitive adhesive polymer are composed of the same monomer units, but the first pressure-sensitive adhesive polymer is crosslinked, and the second pressure-sensitive adhesive polymer is not crosslinked.

In a particularly preferred embodiment, the second pressure-sensitive adhesive polymer is a copolymer of acrylic acid, butyl acrylate, 2-ethylhexylacrylate and vinyl acetate (4.5 to 5.4% acrylic acid, 14.5 to 15.4% butyl acrylate, 75.5 to 76.4% 2-ethylhexylacrylate and 4.5 to 5.4% vinyl acetate), and the first pressure-sensitive adhesive polymer is the corresponding crosslinked polyacrylate. By the crosslinking process some of the carboxylic groups are crosslinked, but some free carboxylic groups remain.

The crosslinker in the preferred crosslinked polymer used as first pressure-sensitive adhesive polymer is aluminium acetyl acetonate, and the weight amount of crosslinker based on the total amount of crosslinked polymer in the most preferred embodiment is about 0.4%. In general, the amount of crosslinker is less than 2%, more preferably less than 1%. Other suitable crosslinkers are known in the art. Suitable crosslinkers are e.g. aluminium acetyl acetonate or polybutyl titanate.

The relative amount of the first adhesive layer (41) and the second adhesive layer (42) in the adhesive layer (4) is not particularly restricted. Preferably, the relative amount of the second adhesive layer is higher than the relative amount of the first adhesive layer (based on the total amount of the adhesive layer, and e.g. the weight ratio of the first adhesive layer to the second adhesive layer is within the range of 0.02 to 2, more preferably 0.05 to 1.3, more preferably 0.05 to 1.0.

Preferably, the area weight of the first adhesive layer (41) is in the range of 2 to 60 g/m$^2$, more preferably 5 to 50 g/m$^2$, more preferably 5 to 40 g/m$^2$ such as about 30 g/m$^2$.

Preferably, the area weight of the second adhesive layer (42) is in the range of 10 to 100 g/m$^2$, preferably 20 to 90 g/m$^2$, more preferably 30 to 70 g/m$^2$ such as 40 g/m$^2$. A preferred range is also 40 to 90 g/m$^2$.

The pressure-sensitive adhesive layer can also contain conventional additives for adhesive layers in active ingredient TTS.

The thickness of the pressure-sensitive adhesive layer (4) (dry thickness) can vary in a range of about 10 µm to about 300 µm, preferably between about 50 µm or 70 µm and about 140 µm. Preferably, in the TTS of the present invention, the pressure-sensitive adhesive layer (4) on the backing layer (5) has a weight of 35 to 150 g/m$^2$, more preferably 40 or 50 to 130 g/m$^2$, and most preferably about 50 g/m$^2$.

Optionally the pressure-sensitive adhesive layer (4), including each of the first (41) and the second adhesive layer (42) can contain additives known to a person skilled in the art to adjust the properties of the polymeric material. Such additives comprise e.g. resins (e.g. ester of hydrogenated rosin), antioxidants (e.g. BHT), plasticizer (e.g. polybuten) etc. (see in part description below).

The separating layer (3) should present a barrier against loss of active ingredient from the polymer matrix layer by diffusion into the adhesive layer and the backing layer. The separating layer of the TTS of the present invention is thus preferably impermeable to the active substance.

The separating layer in the TTS may have a layer thickness of from 5 to 50 µm, preferably from 6 to 15 µm. Suitable barrier polymers to be used as separating layer are polyesters, such as polyethylene terephthalate, polyacrylonitrile, polyvinyl chloride, polyvinylidene chloride or its copolymers or colaminates.

The use of a backing layer made of multidirectional elastic material has been found to be particularly advantageous for the properties and production of the TTS when a non-elastic separating layer is used. Preferably, the TTS of the present invention is therefore a TTS wherein the separating layer (3) is impermeable to the active substance and non-elastic. More preferably, the separating layer (3) is a polyester film that is impermeable to the active substance and non-elastic.

The polymer matrix layer (2) containing an active ingredient also contains a pressure-sensitive adhesive polymer as matrix material. Preferably, the pressure-sensitive adhesive polymer of the polymer matrix layer (2) is a polyacrylate and can be any of the polyacrylates which have been described in connection with the pressure-sensitive adhesive layer (4) above. In one embodiment, the polymer matrix layer contains as polymer matrix material the same pressure-sensitive adhesive that is contained in the first layer (41) of the pressure-sensitive adhesive layer (4).

Preferably, the pressure-sensitive adhesive polymer of the polymer matrix layer (2) of the TTS of the present invention is a crosslinked polyacrylate. It is also preferred that this pressure-sensitive adhesive polymer is a polyacrylate containing acidic groups, which is crosslinked.

To improve the chemical stability of the active ingredient, e.g. of buprenorphine, in the TTS antioxidants may be contained in the polymer matrix layer. Preferred antioxidants here are butylated hydroxytoluene, butyl hydroxyanisol, vitamin C palmitate, tocopherol and its derivatives.

As some active ingredients penetrate through the human skin only in rather limited amounts (such as buprenorphine due to its high molecular weight in combination with a high melting point and very limited solubility in conventional organic solvents and water) suitable permeation enhancers for the active ingredient can be contained in the polymer matrix layer. These can be selected from the group of fatty acids, fatty alcohols, esters of fatty alcohols, esters of fatty acids and mixtures thereof. In one embodiment, the polymer matrix layer contains a fatty acid ester, in particular an ester of oleic acid, an ester of sorbitan, and/or medium- and long-chain fatty acids. These permeation enhancers may advantageously also act as a plasticizer and/or modulate the release of the drug from the TTS.

In one embodiment of the present invention, the polymer matrix layer of the TTS contains oleyl oleate and levulinic acid. Oleyl oleate is e.g. present in an amount of 10 to 20% by weight, preferably 14 to 16% by weight based on the total weight of the polymer matrix layer including the active ingredient. Levulinic acid is e.g. present in an amount of 3 to 15% by weight, preferably 3 to 8% by weight, more preferably 5 to 7% by weight based on the total weight of the polymer matrix layer including the active ingredient.

In one embodiment, the polymer matrix layer also contains a polymer regulator, such as polyvinylpyrrolidone (PVP). The polymer matrix layer of the TTS of the present invention contains PVP preferably in an amount of 5 to 15 weight-%, more preferably 8 to 12 weight-% and most preferably 9 to 11 weight-%, based on the total weight of the polymer matrix layer including the active ingredient.

Preferably, the polymer matrix layer containing an active ingredient has a thickness (dry thickness) in the range of 20 to 400 μm, more preferably in the range of 30 to 200 μm, in particular in the range of 40 to 100 μm.

In one embodiment, the polymer matrix layer of the TTS of the present invention contains 8 to 12 wt.-% buprenorphine base
8 to 12 wt.-% polyvinylpyrrolidone
14 to 16 wt.-% oleyloleate
3 to 8 wt.-% levulinic acid and
55 to 65 wt.-% polyacrylate with carboxylic groups which are crosslinked.

In another embodiment the polymer matrix layer of the TTS of the present invention contains 10 wt.-% buprenorphine base
10 wt.-% polyvinylpyrrolidone
15 wt.-% oleyloleate
6 wt.-% levulinic acid and
59 wt.-% polyacrylate with carboxylic groups which are crosslinked.

It was found that the active ingredient is particularly well stabilized in the described polymer matrix compositions and is advantageous for administering buprenorphine to the skin. However, this polymer matrix is particularly difficult to formulate into a TTS having advantageous adhesive properties, and the present invention allows using the above polymer matrix for administering the active ingredient to the skin of a patient.

In one embodiment, the TTS of the present invention is a TTS wherein the active ingredient is buprenorphine for use in treating pain in a human patient for a dosing interval of at least 3 days, preferably of 7 days. It is particularly relevant for such highly potent and expensive active ingredients such as buprenorphine that TTS production is efficient and the pre-determined dose is delivered reliably. Therefore, the polymer matrix layer containing the active ingredient (or a rate controlling membrane which is located between the polymer matrix layer containing the active ingredient and the skin) must have good contact with the skin to which the active ingredient should be delivered over the entire period the TTS is worn. This must be ensured by the overtape when the polymer matrix layer containing the active ingredient is not sufficiently self-adhesive (e.g. when the polymer matrix layer contains a high amount of active ingredient, such as buprenorphine).

For the production of the TTS according to the present invention, preferably a process comprising the following steps is used:

a) Providing an overtape consisting of a laminate of a backing layer (5) and a pressure-sensitive adhesive layer (4), comprising a first adhesive layer (41) and a second adhesive layer (42) and an intermediate release liner as defined herein as follows: A liquid mass comprising polymer for adhesive layer (41) dissolved in organic solvent(s) is cast onto a first intermediate release liner, the solvent(s) is (are) evaporated by heated air and the dried matrix is laminated with the backing layer (5) yielding a sandwich of the first intermediate release liner, adhesive layer (41) and backing layer (5). Next, a liquid mass comprising polymer for adhesive layer (42) dissolved in organic solvent(s) is cast onto a second intermediate release liner, the solvent(s) is (are) evaporated by heated air and the dried matrix is laminated with the sandwich of adhesive layer (41) and backing layer (5), after removal of the first intermediate release liner so that adhesive layer (41) and adhesive layer (42) combine to yield an overtape consisting a backing layer (5) and a pressure-sensitive adhesive layer (4), comprising a first adhesive layer (41) and a second adhesive layer (42) and the second intermediate release liner.

b) placing individual cores comprising a laminate of a polymer matrix layer (2) containing an active ingredient, and a separating layer (3) one after the other on said release liner (1) with a clearance between said cores and covering said release liner (1) with said overtape under removal of the second intermediate release liner, so that where cores are placed on the release liner (1) the layers are in the order (1), (2), (3), (4), (5); wherein said overtape and said release liner (1) project beyond said cores at all sides thereof, whereafter the overtape is cut by punching in such a manner that the punching line surrounds the external dimensions of the cores, c) removing the resulting latticed refuse of the overtape, and d) then cutting or slitting the release liner (1) in the resultant spaces between the TTS.

The described process is particularly advantageous for the continuous production of TTS in an efficient manner and with reduced (active ingredient-containing) waste.

The release liner (1) is removed before use of the TTS. The release liner (1) is preferably a polymeric material that can optionally be metalized, too. Examples of preferably employed polymeric materials are polyurethanes, polyvinyl acetate, polyvinylidene chloride, polypropylene, polycarbonate, polystyrene, polyethylene, polyethylene terephthalate, polybutylene terephthalate as well as paper optionally surface-coated with the corresponding polymers. Preferably, a release liner that is fluoropolymer-coated or siliconized on one or both side(s) is used. Especially preferred are commercially available fluoropolymer-coated or siliconized polyester films such as the one-sided siliconized commercial products Primeliner 100 μm and Primeliner 75 μm (Loparex, NL).

The materials that can be used for the intermediate release liners are the same as for the release liner (1).

The release liner (1) extends beyond the overtape.

The following examples are intended to illustrate the invention without however limiting it.

EXAMPLE 1

Overtape laminates have been prepared.

Reference Overtape 1 consists of a multidirectionally elastic backing layer made from polyester fabric, a pressure sensitive adhesive layer made from DuroTak® 87-2051 with a nominal area weight of 100 g/m² and a siliconized polyester foil serving as release liner. It was prepared as follows:

A liquid mass of DuroTak® 87-2051 with a solids content of 54% was cast onto a siliconized release liner by means of a standard laboratory coater to achieve a nominal dry area weight of about 100 g/m² (tolerance +/− 10%). The wet film was dried at 80° C. for 20 minutes to quantitatively evaporate the solvents. Afterwards, the dried matrix was laminated with the multidirectionally elastic backing layer.

Overtape 2 consists of a backing layer made from multidirectionally elastic polyester fabric, a pressure sensitive adhesive layer made from DuroTak® 87-2054 with a nominal area weight of 30 g/m² in contact with the backing layer, a second pressure sensitive adhesive layer made from DuroTak® 87-2051 with a nominal area weight of 70 g/m² and a siliconized polyester foil serving as release liner, which is in direct contact with the second pressure sensitive adhesive layer. It was prepared as follows:

A liquid mass of DuroTak® 87-2054 with a solids content of 48% was cast onto a siliconized release liner by means of a standard laboratory coater to achieve a nominal dry area weight of about 30 g/m² (tolerance +/− 10%). The wet film was dried at 80° C. for 20 minutes to quantitatively evaporate the solvents. Afterwards, the dried matrix was laminated with the multidirectionally elastic backing layer to result in intermediate overtape laminate 1.

In a second step, a liquid mass of DuroTak® 87-2051 with a solids content of 48% was cast onto a siliconized release liner by means of a standard laboratory coater to achieve a nominal dry area weight of about 70 g/m² (tolerance +/− 10%). The wet film was dried at 80° C. for 20 minutes to quantitatively evaporate the solvents. Afterwards, the release liner was removed from intermediate overtape laminate 1, and the remaining sandwich of intermediate overtape laminate 1 comprising the multidirectionally elastic backing layer and the adhesive matrix made from DuroTak® 87-2054 was laminated onto the adhesive matrix made from DuroTak® 87-2051, so that both adhesive matrices get in contact and result in the described assembly of overtape 2.

Overtape 3 consists of a backing layer made from multidirectionally elastic polyester fabric, a pressure sensitive adhesive layer made from styrenic rubber DuroTak® 87-6911 with a nominal area weight of 40 g/m² in contact with the backing layer, a second pressure sensitive adhesive layer made from DuroTak® 87-2051 with a nominal area weight of 60 g/m² and a siliconized polyester foil serving as release liner, which is in direct contact with the second pressure sensitive adhesive layer. It was prepared in the same manner as described for Overtape 2.

Overtape 4 consists of a backing layer made from unidirectional elastic polyester fabric, a pressure sensitive adhesive layer made from styrenic rubber DuroTak® 87-6911 with a nominal area weight of 20 g/m² in contact with the backing layer, a second pressure sensitive adhesive layer made from DuroTak® 87-2051 with a nominal area weight of 30 g/m² and a siliconized polyester foil serving as release liner, which is in direct contact with the second pressure sensitive adhesive layer. It was prepared in the same manner as described for Overtape 2.

Overtape 5 consists of a backing layer made from unidirectional elastic polyester fabric, a pressure sensitive adhesive layer made from styrenic rubber DuroTak® 87-6911 with a nominal area weight of 30 g/m² in contact with the backing layer, a second pressure sensitive adhesive layer made from DuroTak® 87-2051 with a nominal area weight of 40 g/m² and a siliconized polyester foil serving as release liner, which is in direct contact with the second pressure sensitive adhesive layer. It was prepared in the same manner as described for Overtape 2.

Overtape 6 consists of a backing layer made from unidirectional elastic polyester fabric, a pressure sensitive adhesive layer made from polyisobutylene (1:1 mixture of Oppanol B10 SNF and Oppanol B100) with a nominal area weight of 30 g/m² in contact with the backing layer, a second pressure sensitive adhesive layer made from DuroTak® 87-2051 with a nominal area weight of 40 g/m² and a siliconized polyester foil serving as release liner, which is in direct contact with the second pressure sensitive adhesive layer. It was prepared in the same manner as described for Overtape 2.

The overtapes of the invention were tested for reduction of adhesive strength over time in comparison to the reference Overtape 1 according ASTM D3330/D3330M-04 (2010)-"Standard Test Method for Peel Adhesion of Pressure-Sensitive Tape (Method F, 90° C.)":

| Overtape | Initial Adhesive strength | Adhesive strength after 2 weeks |
|---|---|---|
| 1 | 6.2 N/25 mm | 2.1 N/25 mm (ambient conditions)<br>0.1 N/25 mm (40° C.) |
| 2 | 8.7 N/25 mm | 8.1 N/25 mm (ambient conditions)<br>4.8 N/25 mm (40° C.) |

The data show that adhesive strength of the overtape consisting of two pressure sensitive adhesive layers is maintained over time. The overtape one comprising only one pressure sensitive adhesive cannot maintain adhesive strength.

EXAMPLE 2

Transdermal patches with the following composition have been prepared as follows:

An API containing core laminate was prepared out of an adhesive coating mass containing the components as described in the table below. Additionally, ethanol and ethylacetate were added to properly dissolve all components and to adjust the solids content of the coating mass to a defined value. Afterwards, the uniform coating mass was cast onto a siliconized release liner and the solvents were quantitatively evaporated to yield a dried laminate with the qualitative and quantitative composition provided in the table below. The dried matrix was covered with a polyester foil serving as separating layer.

A backing layer laminate was manufactured as follows: A liquid mass made from DuroTak® 87-2054 was cast onto a first intermediate release liner, the solvents were evaporated by heated air and the dried matrix was laminated with the multidirectionally elastic backing layer to yield intermediate overtape laminate 1.

Next, a liquid mass made from DuroTak® 87-2051 was cast onto a second intermediate release liner, the solvents were evaporated by heated air and the dried matrix was laminated with the sandwich of intermediate overtape laminate 1, from which the release liner was removed, in a manner that the adhesive matrix made from DuroTak® 87-2054 combines with adhesive matrix made from DuroTak® 87-2051.

In a next step individual cores sized 25 cm² made from API containing laminate and comprising the API containing matrix and the separating layer were placed onto a siliconized release liner so that the distance between two cores was at least 32.5 mm. Afterwards the cores were covered with the backing layer laminate, which was freed from its release liner, so that the adhesive side of the backing layer laminate contacts the separating layer of the active cores, and in between said siliconized release liner. Afterwards, patches sized 51 cm² were die cut from this laminate assembly, so that the active core is centrally situated in the backing layer laminate segment. The individual patches were sealed into sachets made of multilaminate foil

| Composition Table: | |
|---|---|
| Material | Concentration |
| PI-containing core | |
| Buprenorphine | 10% |
| Polyvinylpyrrolidone | 10% |
| Oleyl oleate | 15% |
| Levulinic acid | 6% |

-continued

Composition Table:

| Material | Concentration |
|---|---|
| Polyacrylate with carboxylic groups (crosslinked) | 59% |
| Matrix area weight | 80 g/m² |
| Overtape | |
| First layer: Polyacrylate with carboxylic groups (crosslinked), 30 g/m² | 100% |
| Second layer: Polyacrylate with carboxylic groups, 70 g/m² | 100% |
| Total Matrix area weight | 100 g/m² |

Adhesive strength has been measured initially and after one month of storage at 40° C./75% relative humidity (patches individually sealed into multi laminate sachets with aluminum barrier foil). Adhesive strength was 3.0 N/25 mm in both analysis. These data show suitability of overtape laminate with two pressure sensitive adhesive layers within scope of the present invention, if combined with an active drug containing core.

It is evident from this specification that the term "different" in connection with polymers refers to any difference which can distinguish these polymers from each other, such as molecular weight or monomer composition, or type of monomer or crosslinking status.

The invention claimed is:

1. A transdermal therapeutic system comprising
   a) a release liner,
   b) a core comprising
      b1) a polymer matrix layer containing an active ingredient and
      b2) a separating layer
   and
   c) an overtape comprising
      c1) a pressure-sensitive adhesive layer and
      c2) a backing layer
wherein the overtape c) and the release liner extend beyond the core at all sides of the core, wherein the pressure-sensitive adhesive layer comprises a first layer which is in contact with the backing layer and comprises a first pressure-sensitive adhesive polymer, and a second layer which is in contact with the first layer on one side over the full surface area and with the release liner on the other side and comprises a second pressure-sensitive adhesive polymer, wherein the second pressure-sensitive adhesive polymer is non-crosslinked polyacrylate and the first pressure-sensitive adhesive polymer is a crosslinked polyacrylate that has a lower adhesiveness than the second pressure-sensitive adhesive polymer.

2. The transdermal therapeutic system according to claim 1, wherein the second pressure-sensitive adhesive polymer is a non-crosslinked polyacrylate with carboxyl groups.

3. The transdermal therapeutic system according to claim 1, wherein the pressure-sensitive adhesive layer and the backing layer extend at least 4 mm beyond the core.

4. The transdermal therapeutic system according to claim 1, wherein the active ingredient is an opioid or a pharmaceutically acceptable salt thereof.

5. The transdermal therapeutic system according to claim 4, wherein the active ingredient is buprenorphine.

6. The transdermal therapeutic system according to claim 1, wherein the backing layer is unidirectional or multidirectional elastic.

7. The transdermal therapeutic system according to claim 1, wherein the backing layer comprises a polyester polymer.

8. The transdermal therapeutic system according to claim 1, wherein the area weight of the first adhesive layer is in the range of 5 g/m² to 40 g/m² and the area weight of the second adhesive layer is in the range of 20 g/m² to 90 g/m².

9. The transdermal therapeutic system according to claim 1, wherein the first pressure-sensitive adhesive polymer is a crosslinked polyacrylate which comprises carboxyl groups.

10. The transdermal therapeutic system according to claim 1, wherein the separating layer is a polyester film which is impermeable to the active ingredient.

11. The transdermal therapeutic system according to claim 1, wherein the polymer-matrix layer contains
    8 to 12 wt.-% buprenorphine base
    8 to 12 wt.-% polyvinylpyrrolidone
    14 to 16 wt.-% oleyloleate
    3 to 8 wt.-% levulinic acid and
    55 to 65 wt.-% crosslinked polyacrylate.

12. The transdermal therapeutic system according to claim 11, wherein the polymer-matrix layer contains
    10 wt.-% buprenorphine base
    10 wt.-% polyvinylpyrrolidone
    15 wt.-% oleyloleate
    6 wt.-% levulinic acid and
    59 wt.-% crosslinked polyacrylate.

13. The transdermal therapeutic system according to claim 1, wherein the active ingredient is buprenorphine for use in treating pain in a human patient with a dosing interval of at least 3 days.

14. The transdermal therapeutic system according to claim 3, wherein the pressure-sensitive adhesive layer and the backing layer extend 4 mm to 30 mm beyond the core.

15. The transdermal therapeutic system according to claim 3, wherein the pressure-sensitive adhesive layer and the backing layer extend 6 mm to 15 mm beyond the core.

16. The transdermal therapeutic system according to claim 8, wherein the area weight of the second adhesive layer is in the range of 40 g/m² to 90 g/m².

17. A process for the production of a transdermal therapeutic system according to claim 1 comprising
    a) providing an overtape consisting of a laminate of a backing layer and a pressure-sensitive adhesive layer, wherein the pressure-sensitive adhesive layer comprises a first adhesive layer and a second adhesive layer according to claim 1; and an intermediate release liner; adhesive layer, comprising a first adhesive layer and a second adhesive layer as defined in claim 1 and an intermediate release liner;
    and
    b) placing individual cores comprising a laminate of a polymer matrix layer containing an active ingredient, and a separating layer, one after the other on said release liner with a clearance between said cores, removing the intermediate release liner from the product of step a) and covering said release liner with said overtape wherein when the cores are placed on the release liner the layers are arranged in the order: i) release liner, ii) polymer matrix layer, iii) separating layer, iv) pressure-sensitive adhesive layer and v) backing layer; wherein said overtape and said release liner project beyond said cores at all sides thereof, whereafter the overtape is cut by punching resulting in a punching line surrounding the external dimensions of the cores,
    c) removing the resulting latticed refuse of the overtape, and d) then cutting the release liner in the resultant spaces between the cores.

18. The transdermal therapeutic system according to claim 13, wherein the active ingredient is buprenorphine for use in treating pain in a human patient with a dosing interval of at least 7 days.

* * * * *

UNITED STATES PATENT AND TRADEMARK OFFICE
CERTIFICATE OF CORRECTION

PATENT NO. : 11,013,697 B2  
APPLICATION NO. : 15/549185  
DATED : May 25, 2021  
INVENTOR(S) : Björn Schurad et al.

Page 1 of 1

It is certified that error appears in the above-identified patent and that said Letters Patent is hereby corrected as shown below:

In the Claims

In Claim 1 (Column 15, Lines 49-50), the "a" is missing before the term "non-cross-linked polyacrylate".

In Claim 17 (Column 16, Lines 47-49), step a) delete "adhesive layer, comprising a first adhesive layer and a second adhesive layer as defined in claim 1 and an intermediate release liner;".

Signed and Sealed this  
Third Day of August, 2021

Drew Hirshfeld  
*Performing the Functions and Duties of the*  
*Under Secretary of Commerce for Intellectual Property and*  
*Director of the United States Patent and Trademark Office*